United States Patent [19]

Leeming et al.

[11] 4,193,994

[45] Mar. 18, 1980

[54] TETRAHYDRO-S-TRIAZINE THIONES

[75] Inventors: Michael R. G. Leeming, Canterbury; Subramaniyan Narayanaswami, Deal; Alexander B. Penrose, Tilmanstone, Nr. Deal, all of England

[73] Assignee: Pfizer Inc., New York, N.Y.

[21] Appl. No.: 921,204

[22] Filed: Jul. 3, 1978

[30] Foreign Application Priority Data

Jul. 22, 1977 [GB] United Kingdom ............... 30998/77

[51] Int. Cl.$^2$ ...................... C07D 251/08; A01N 9/12
[52] U.S. Cl. ...................................... 424/249; 544/220
[58] Field of Search .......................... 424/249; 544/220

[56] References Cited

U.S. PATENT DOCUMENTS

| | | | |
|---|---|---|---|
| 3,505,057 | 4/1970 | Luckenbaugh | 544/220 |
| 3,505,323 | 4/1970 | Luckenbaugh | 544/220 |

OTHER PUBLICATIONS

Burke, J. Amer. Chem. Soc., vol. 69, pp. 2136–2137 (1947).

*Primary Examiner*—John M. Ford
*Attorney, Agent, or Firm*—Connolly & Hutz

[57] ABSTRACT

A series of tetrahydro-s-triazin-2-[1H]-thiones and their use as acaricidal agents.

15 Claims, No Drawings

TETRAHYDRO-S-TRIAZINE THIONES

BACKGROUND OF THE INVENTION

1. Field of the Invention

This invention relates to novel 1-(O-tolyl)-3,5-disubstituted-tetrahydro-s-triazin-2[1H]-thiones, their use as acaricidal agents and a composition thereof.

2. Description of the Prior Art

The synthesis of tetrahydro-s-triazin-2[1H]-thiones are known in the art. Burke, *J. Am. Chem. Soc.*, 69, 2136 (1947) reported the reaction of thiourea with formaldehyde and amines. More recently U.S. Pat. Nos. 3,505,057 and 3,505,323 have reported the synthesis of 1-aryl-tetrahydro-s-triazin-2[1H]-thiones and their use as herbicidal agents.

SUMMARY OF THE INVENTION

The acaricidal agents of the present invention are represented by the formula

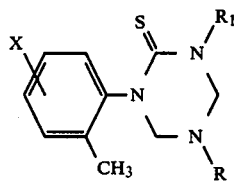

and a pharmaceutically acceptable acid addition salt thereof,
wherein
R is alkyl of one to twelve carbon atoms, cycloalkyl of three to six carbon atoms, adamantyl, benzyl, allyl, propargyl or substituted alkyl wherein said alkyl contains two to four carbon atoms and said substituent is hydroxy, alkoxy of one to three carbon atoms, alkanoyloxy of two to five carbon atoms, methylamino, dimethylamino, phenyl, p-toluenesulfonyloxy or carbamoyloxy of the formula

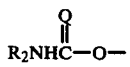

wherein $R_2$ is hydrogen, cyclohexyl, phenyl or methyl and Q is sulphur or oxygen with the proviso that said substituent is substituted on other than the alpha-position of said substituted alkyl group;
$R_1$ is alkyl of one to three carbon atoms or hydroxymethyl; and
X is hydrogen or alkyl of one to three carbon atoms.

Also part of this invention is a method for protecting cattle from acarids which comprises applying externally to said cattle in need of such protection an acaricidal amount of a compound of formula I, and a pharmaceutically acceptable acid addition salt thereof wherein R, $R_1$ and X are as defined, and an acaricidal composition comprising an effective amount of a compound of formula I, and a pharmaceutically acceptable acid addition salt wherein R, $R_1$ and X are as defined together with a diluent or carrier.

A preferred group of compounds useful as acaricidal agents are those of formula I wherein $R_1$ is methyl and R is alkyl of one to twelve carbon atoms.

Particularly preferred within this group of compounds are 1-(2,4-dimethylphenyl)-3,5-dimethyl-tetrahydro-s-triazin-2[1H]-thione, 1-(2,4-dimethylphenyl)-3-methyl-5-i-propyl-tetrahydro-s-triazin-2[1H]-thione and 1-(2,4-dimethylphenyl)-3-methyl-5-t-butyl-tetrahydro-s-triazin-2[1H]-thione.

DETAILED DESCRIPTION OF THE INVENTION

The compounds of the formula (I) where $R_1$ is alkyl can be prepared from a substituted thiourea of the formula (II) and an amine $RNH_2$ in the presence of formaldehyde according to the following equation:

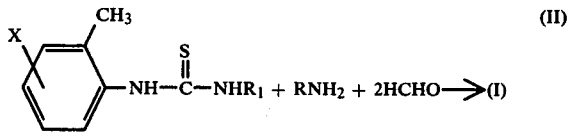

wherein R and X are as previously defined and $R_1$ is alkyl.

The reaction is generally performed in the presence of an aqueous organic solvent, e.g. aqueous dioxan, aqueous propanol or aqueous ethylene glycol and can conveniently be carried out by adding the amine to excess aqueous formaldehyde solution and then adding the thiourea, preferably as a solution in an organic solvent e.g. dioxan. The reaction can be performed at a temperature between room temperature and the reflux temperature of the solvent and may take from several hours to several days to complete depending on the nature of the reactants and the temperature employed. We have found that the reaction is preferably performed at a temperature of 45°–50° C. to avoid the decomposition and formation of biproducts which sometimes occurs at higher temperatures, and generally takes two to three days to go substantially to completion at this temperature.

In other cases, for example, where $R_1$ and R are alkyl groups (e.g. methyl groups) the reaction can with advantage be performed at a higher temperature e.g. by heating on a steam bath, and in this case the reaction is generally complete within 1½ to 3 hours. In some instances the product crystallizes on cooling the solution; otherwise, the product is conveniently isolated by evaporation of the solvent or alternatively by adding a large excess of water to precipitate the product which is collected by filtration or by extraction into an organic solvent, e.g. diethyl ether, and removal of the solvent. In either case the crude product may be further purified, if desired, by conventional techniques e.g. by recrystallization or by chromatography. Compounds of the formula (I) wherein R is an alkyl group substituted with an alkanoyloxy group can also be prepared by acylation of the corresponding hydroxy alkyl substituted compound e.g. using the acid chloride. Compounds of the formula (I) wherein R is an alkyl group substituted with a carbamoyloxy, thiocarbamoyloxy or N-substituted-carbamoyloxy or thiocarbamoyloxy group can similarly be prepared from the corresponding hydroxy alkyl substituted compound using potassium isocyanate or isothiocyanate or an appropriate alkyl, cyclohexyl or phenylisocyanate or isothiocyanate respectively. Compounds of the formula (I) wherein R is an alkyl group substituted with an aryl-sulphonyloxy group can also be prepared from the corresponding hydroxy alkyl compound by sulphonylation e.g. using a sulphonyl chloride.

Compounds of the formula (I) wherein $R_1$ is a hydroxy-methyl group can be prepared from the compound of the formula (I) wherein $R_1$ is hydrogen, prepared as indicated above using a thiourea of the formula (II) wherein $R_1$ is hydrogen. Thus, reaction with formaldehyde yields the compound of formula (I) wherein $R_1$ is a hydroxy-methyl group.

The pharmaceutically acceptable acid addition salts of the compounds of the formula (I) can be made in a conventional manner, e.g. by mixing a solution of the free base in a suitable solvent, e.g. diethyl ether, with a solution of the appropriate acid, e.g. hydrochloric acid, in a suitable solvent, e.g. diethyl ether, and recovering the salt as a precipitate.

The starting thioureas of formula (II) are known compounds and they can be readily prepared by conventional reactions. For example the preparation of the compound of formula (II) wherein $R_1$ and X are each a methyl group is described in *J. Chem. Soc.*, (1929) 945. Other compounds of formula (II) can be prepared in a similar manner by reaction of an appropriately ring substituted aniline derivative with an alkyl isothiocyanate. If desired the starting thiourea need not be isolated but the crude reaction mixture can be treated directly with formaldehyde and the amine of formula $RNH_2$ to give the final product of formula (I) in a single step.

The amines of formula $RNH_2$ are all readily available compounds.

The compounds of the formula (I) have acaricidal activity, particularly against all stages in the life cycle, including gravid female ticks, of the cattle ticks *Boophilus microplus*, *Haemaphysalis longicornus*, *Rhipicephalus appendiculatus* and *Boophilus decoloratus*.

In one test, five freshly collected, fully engorged *Boophilus microplus* adult female ticks are used for each acaricidal compound. Using a micro-pipette 10 microliters of a solution containing 10 micro-grams of the acaricidal compound in ethanol or acetone, is applied to the dorsal surface of each of the ticks. The treated ticks are placed in weighed 1"×2" glass vials, weighed and stored at 26° C. and 80% relative humidity in plastic boxes for two weeks. The ticks were then removed from the vials and the vials weighed to give the weight of eggs laid by the ticks. Any reduction in the egg laying of the treated ticks is calculated as a percentage of the eggs laid by untreated control ticks.

The eggs are returned to the incubator for a further 3 weeks after which time the percentage of eggs hatching is estimated. The percentage effect is calculated as the overall reduction in the anticipated reproduction of the ticks using the weight of eggs laid and the percentage of eggs hatching. The test may be repeated using smaller amounts of the acaricidal compound.

In another test, using a pipette 0.5 ml of a solution containing 0.5 mg of the acaricidal compound in ethanol or acetone is spread evenly on to a Whatman No. 1 filter paper 8 cm×6.25 cm (50 sq. c.m.) to give a dosage of 100 mg/m². The treated paper is allowed to dry to room temperature, folded with the treated surface inside and the two short edges sealed with a crimping machine. The open ended envelope is placed in a 11*b* Kilner jar containing damp cotton wool in a plastic pot and stored in an incubator at 26° C. for 24 hours. 20–50 *Boophilus microplus* larvae, which had hatched 8–14 days previously are placed in the envelope using a small spatula. The open end is then crimped to form a sealed packet. The treated paper containing the larvae is returned to the Kilner jar and kept for a further 48 hours in the incubator. 20–50 larvae are placed similarly in an untreated paper envelope to act as controls. At the end of the 48 hour test period the mortality is noted and recorded as a percentage after correction for any mortality among the untreated control ticks.

The test can be repeated using smaller amounts of the acaricidal compound.

In addition to percentage effectiveness figures, $ED_{50}$ results can be obtained from dose response measurements using any of the afore-described tests.

Activity against *Haemaphysalis longicornus* nymphs can be measured in a similar manner to the above larvae test.

The activity of certain of the compounds of the Examples detailed hereinafter against the tick *Boophilus microplus* is set out in the following Table:

TABLE I

| Acaricidal Activity vs. Adult *Boophilus microplus* (topical application) | |
|---|---|
| Example No. | % Effect at 10 μg |
| 1 | 100 |
| 2 | 99 |
| 3 | 100 |
| 4 | 100 |
| 5 | 100 |
| 6 | 100 |
| 7 | 99 |
| 8 | 68 |
| 9 | 86 |
| 10 | 100 |
| 11 | 100 |
| 12 | 95 |
| 13 | 58 |
| 14 | 100 |
| 15 | 28 |
| 16 | 78 |
| 17 | 93 |
| 18 | 94 |
| 19 | 74 |
| 20 | 63 |
| 21 | 47 |
| 22 | 100 |
| 23 | 89 |
| 24 | 10 |
| 25 | 49 |
| 26 | 25 |
| 27 | 100 |
| 28 | 80 |
| 29 | 35 |

Thus the invention also provides an acaricidal composition comprising an effective amount of a compound of the formula (I) or a pharmaceutically acceptable acid addition salt thereof together with a diluent or carrier. The diluent or carrier may be a solid or a liquid, optionally together with an antioxidant, dispersing agent, emulsifying agent or wetting agent. The compositions of the invention include not only compositions in a suitable form for application but concentrated primary compositions which may be supplied to the user and which require dilution with a suitable quantity of water or other diluent prior to application. Typical compositions of the invention include, for example, dusting powders, dispersible powders, solutions, dispersions, emulsions and emulsifiable concentrates.

A dust can be made by mixing the appropriate amount of the finely divided active compound with a solid pulverulent diluent or carrier such as talc, clay, calcite, pyrophyllite, diatomaceous earth, walnut shell flour, silica gel, hydrated alumina, or calcium silicate. As an alternative method of preparation, the diluent or carrier is mixed with a solution of the active compound in a volatile organic solvent such as toluene, the solvent being subsequently removed by evaporation. Typically, the active compound will be present in the dust in an amount of from 0.25 to about 4% by weight.

Dispersible powders of special value for spray applications can be made by adding a suitable dispersing agent to the active compound, or to a dust containing the active compound, so that a stable aqueous dispersion of the active compound is formed on mixing the powder with water. The dispersible powders preferably contain from about 25 to 75% by weight of the active compound.

Emulsifiable concentrates comprise a solution of the active compound in a substantially water-immiscible nontoxic organic solvent containing an emulsifying agent. Suitable solvents include, for example, toluene, xylene, petroleum oil, and alkylated naphthalenes. Preferably, the concentrate will contain 5-75 gms of the active compound per 100 ml of solution. The concentrates can be diluted with water prior to use to give a typical concentration of the active compound in the aqueous medium of from e.g. about 0.01 to about 0.1% w/v (g/100 ml), or approximately 100 to 1000 ppm. The volatile solvents, e.g. toluene and xylene, evaporate after spraying to leave a deposit of the active ingredient. The made up spray or dip will generally be an emulsion.

The compositions of the invention can be applied to ground, such as that around dairies, in order to combat e.g. cattle ticks, thereon. However, it is preferred to treat animals by spraying them or passing them through animal dips.

Thus the present invention also provides a method for protecting animals, particularly cattle, from acarids, particularly cattle ticks, which comprises treating the animal externally with an acaricidal amount of a compound of the formula (I) or acaricidal composition as defined above.

The compositions of the invention may also contain a pesticide, fungicide, additional acaricide, or the like.

The invention is illustrated by the following Examples.

EXAMPLE 1 t-Butylamine (0.88 g, 12 mmole) was added dropwise with stirring to a cooled 37% solution of aqueous formaldehyde (20 ml). After 15 minutes a warm solution of N-2,4-dimethylphenyl N'-methyl thiourea (1.94 g, 10 mmole) in dioxan (5 ml) was added and the mixture was warmed at 45° to 50° C. for 48 hours. The solvent was removed by evaporation under reduced pressure to yield an oil which was washed with water and then extracted with methylene chloride (2×50 ml). The extracts were combined, dried over $MgSO_4$ and evaporated. The residue was taken up in diethyl ether (20 ml) and cooled to yield a crystalline precipitate which was collected by filtration, washed with a little cold hexane and dried under vacuum to give 5-t-butyl-1-(2,4-dimethylphenyl)-3-methyl-tetrahydro-s-triazin-2[1H]-thione as a white crystalline solid (1.35 g, 46%), m.p. 111°–112° C. Found: C, 66.4, H, 9.0, N, 14.6%. $C_{16}H_{25}N_3S$ requires: C, 66.0, H, 8.6, N, 14.4%. m/e found 291, required 291.

EXAMPLE 2

A solution of 2,4-xylidine (121 g, 90% purity) in ethylene glycol (195 ml) was added over five minutes to a mixture of methylisothiocyanate (73 g) in ethylene glycol (195 ml) and the mixture was stirred and heated on a steam bath for ½ hour. Aqueous formaldehye solution (330 ml of 37%) was then added over five minutes followed by aqueous methylamine solution (230 ml of 25% weight/volume) and the reaction mixture was again stirred and heated on the steam bath for a further 1½ hours.

The resulting clear solution was allowed to cool to room temperature with stirring, the resulting crystalline precipitate was collected by filtration, washed with water and dried. Recrystallization from chloroform/hexane gave 1-(2,4-dimethylphenyl)-3,5-dimethyl-terahydro-s-triazin-2[1H]-thione (200 g, 87% yield), m.p. 107°–108° C. Found: C, 62.7, H, 7.7, N, 17.0. $C_{13}H_{19}N_3S$ requires C 62.3, H, 7.6, N, 16.9%. m/e found 249, required 249.

EXAMPLES 3-20

The following tetrahydro-s-triazin-2[1H]-thiones were prepared by the general method of Example 1 starting with the appropriate thiourea and amine.

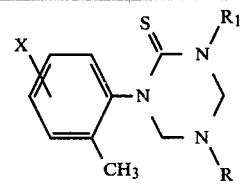

| Example No. | $R_1$ | R | X | m.p. °C. | Analysis % (Theoretical in brackets) C | H | N |
|---|---|---|---|---|---|---|---|
| 3 | $CH_3$ | $CH_2CH_2OH$ | 4-$CH_3$ | 101–2 | 60.1 (60.2) | 7.55 7.5 | 14.9 15.1) |
| 4 | $CH_3$ | $CH(CH_3)_2$ | 4-$CH_3$ | 113–4 | 64.8 (65.0) | 8.3 8.3 | 15.1 15.2) |
| 5 | $CH_3$ | cyclohexyl | 4-$CH_3$ | 100–1 | 68.1 (68.1 | 8.6 8.5 | 13.4 13.3) |
| 6 | $CH_3$ | $CH_2CH_3$ | 4-$CH_3$ | oil | 63.1 (63.9 | 8.1 8.0 | 15.3 16.0) |
| 7 | $CH_3$ | $CH_2CH=CH_2$ | 4-$CH_3$ | 76–7 | 65.6 (65.4 | 7.9 7.6 | 15.0 15.3) |

-continued

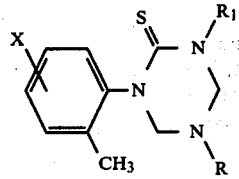

| Example No. | $R_1$ | R | X | m.p. °C. | Analysis % (Theoretical in brackets) C | H | N |
|---|---|---|---|---|---|---|---|
| 8 | $CH_3$ | $CH_2$-phenyl | 4-$CH_3$ | 124–5 | 70.4 (70.1 | 7.4 7.1 | 13.2 12.9) |
| 9 | $CH_2CH_3$ | $CH_3$ | 4-$CH_3$ | 78–9 | 63.6 (63.9 | 8.0 8.0 | 15.9 16.0) |
| 10 | $CH_3$ | $CH_2CH_2$-phenyl | 4-$CH_3$ | glass | 70.5 (70.8 | 7.3 7.4 | 12.7 12.4) |
| 11 | $CH_3$ | $(CH_2)_3CH_3$ | 4-$CH_3$ | oil | 66.0 (65.6 | 8.6 9.1 | 14.4 14.4) |
| 12 | $CH_3$ | $-CH_3$ | H | 120–1 | 60.8 (61.2 | 7.5 7.3 | 18.1 17.9) |
| 13 | $CH_3$ | $-CH_3$ | 3-$CH_3$ | 186–7 | 62.4 (62.6 | 7.8 7.7 | 16.9 16.9) |
| 14 | $CH_3$ | $-CH_3$ | 6-$CH_3$ | 121–2 | 62.7 (62.6 | 7.9 7.7 | 17.1 16.9) |
| 15 | $CH_2CH_3$ | $-CH_2CH_3$ | 4-$CH_3$ | oil | — | — | — |
| 16 | $CH_3$ | $-(CH_2)_{11}CH_3$ | 4-$CH_3$ | oil | 71.5 (71.5 | 10.4 10.2 | 10.7 10.4) |
| 17 | $CH_3$ | $-(CH_2)_9CH_3$ | 4-$CH_3$ | oil | 70.25 (70.4 | 10.0 9.9 | 11.6 11.2) |
| 18 | $CH_3$ | adamantyl | 4-$CH_3$ | 151–2 | 71.4 (71.2 | 8.6 8.9 | 11.3 11.3) |
| 19 | $CH_3$ | $-(CH_2)_5CH_3$ | 4-$CH_3$ | oil | 67.6 (67.7 | 9.5 9.1 | 13.2 13.2) |
| 20 | $CH_3$ | $-(CH_2)_3OH$ | 4-$CH_3$ | 110–115 | 60.6 (61.4 | 7.7 7.8 | 13.0 14.3) |

EXAMPLE 21

Formaldehyde (4.86 g, 37% solution, 30 mmole) was added to a solution of 2,4-dimethyl-phenyl thiourea (4.5 g, 24 mmole) in dimethylformamide (40 ml) and the solution was stirred for 15 minutes at room temperature. Methylamine (3.72 g, 30 mmole) was added dropwise with stirring and the mixture was heated under reflux at 100° C. for 4 hours. The solution was cooled and the solvent removed under vacuum to yield an oil. This was diluted with diethyl-ether and refrigerated to yield 1-(2,4-dimethylphenyl)-5-methyl-tetrahydro-s-triazin-2[1H]-thione as a white crystalline solid which was collected, washed with a little cold diethyl ether and dried (4.5 g, 77%), m.p. 140°–143° C.

The product (1.18 g, 5 mmole) was dissolved in dioxan (5 ml) with warming, the solution cooled to room temperature and formaldehyde (0.41 g, 37% solution, 5 mmole) added. The solution was kept at 45° C. for 6 weeks. The solvent was then removed under vacuum and the product was washed with water, dissolved in dichloromethane, dried over $MgSO_4$ and the solvent evaporated to yield a clear oil which solidified on stirring with diethyl ether (50 ml). The product was recrystallized from a mixture of hexane and dichloromethane to yield 1-(2,4-dimethylphenyl)-3-hydroxymethyl-5-methyl-tetrahydro-s-triazin-2[1H]-thione as a white crystalline solid (0.40 g, 30%), m.p. 121°–122° C.

Analysis %: Found: C, 58.5; H, 7.1; N, 15.65 $C_{13}H_{19}N_3O_5$ requires: C, 58.9; H, 7.2; N, 15.85%.

EXAMPLE 22

Acetyl chloride (0.168 g, 1.5 mmole) was added dropwise with stirring to a cooled solution of 1-(2,4-dimethylphenyl)-5-(2-hydroxyethyl)-3-methyl-tetrahydro-s-triazin-2[1H]-thione (0.60 g, 1 mmole) in dry toluene (30 ml). After 10 minutes the solution was allowed to warm to room temperature and stirring was continued for a further 3 hours. The solution was filtered and the solvent removed under vacuum. The product was chromatographed on a column of silica eluting with dichloromethane containing 2% methanol to yield an oil. Trituration with diethyl ether gave 5-(2-acetoxyethyl)-1-(2,4-dimethylphenyl)-3-methyl-tetrahydro-s-triazin-2[1H]-thione (0.24 g, 35%), m.p. 80°–83° C.

Analysis %: Found: C, 59.7; H, 7.3; N, 12.95 $C_{16}H_{23}N_3O_2S$ requires: C, 59.8; H, 7.2; N, 13.1%.

EXAMPLE 23

The method of Example 22 was followed using pivaloyl chloride to give 1-(2,4-dimethylphenyl)-3-methyl-5-(2-pivaloyloxyethyl)-tetrahydro-s-triazin-2[1H]-thione as an oil.

Analysis %: Found: C, 62.35; H, 8.1; N, 10.9 $C_{19}H_{29}N_3O_2S$ requires: C, 62.8; H, 8.0; N, 11.6%.

EXAMPLE 24

Phenylisocyanate (0.62 g, 5.2 mmole) was added to a stirred solution of 1-(2,4-dimethylphenyl)-5-(2-hydroxyethyl)-3-methyl-tetrahydro-s-triazin-2[1H]-thione (1.0 g, 3.5 mmoles) and triethylamine (0.31 g, 5.2 mmole) in dry toluene (40 ml). The mixture was stirred at room temperature for 2 hours and the solvent was then removed under vacuum and the residual gum triturated with petroleum ether (b.p. 60°-80° C.) to yield 1-(2,4-dimethylphenyl)-3-methyl-5-(2-N-phenyl-carbamoyloxyethyl)-tetrahydro-s-triazin-2[1H]-thione (1.18 g, 84%), m.p. 60°-65° C.

Analysis %: Found: C, 64.0; H, 6.6; N, 13.5 $C_{21}H_{26}N_4O_2S$ requires: C, 63.3; H, 6.5; N, 14.1.

EXAMPLE 25

The method of Example 24 was followed using methylisocyanate to give 1-(2,4-dimethylphenyl)-3-methyl-5-(2-N-methyl-carbamoyloxyethyl)-tetrahydro-s-triazin-2-[1H]-thione, m.p. 110°-113° C.

Analysis %: Found: C, 57.0; H, 7.2; N, 16.8 $C_{16}H_{24}N_4O_2S$ requires: C, 57.1; H, 7.1; N, 16.7%.

EXAMPLE 26

A solution of 1-(2,4-dimethylphenyl)-5-(2-hydroxyethyl)-3-methyl-tetrahydro-s-triazin-2[1H]-thione (1.0 g, 3.6 mmole) in dimethylformamide (10 ml) was added slowly to a stirred suspension of sodium hydride (0.172 g, 3.6 mmole as 50% dispersion in oil) at room temperature.

When evolution of hydrogen had ceased a solution of cyclohexyl isothiocyanate (0.74 g, 5.3 mmole) in dimethylformamide (5 ml) was added slowly and the mixture was stirred at room temperature for 3 hours. The solution was then poured into water (50 ml) and the product extracted into ether. The ether layer was separated, washed with water, dried and the solvent removed to yield an oil. Trituration with petroleum ether (b.p. 60°-80° C.) gave 5-(2-N-cyclohexyl-thiocarbamoyloxyethyl)-1-(2,4-dimethylphenyl)-3-methyl-tetrahydro-s-triazin-2[1H]-thione as a white solid (0.18 g, 12%), m.p. 68°-72° C.

Analysis %: Found: C, 59.8; H, 7.7; N, 13.1 $C_{16}H_{24}N_4OS_2$ requires: C, 60.1; H, 7.4; N, 13.4.

EXAMPLE 27

The method of Example 26 was followed using methyl isothiocyanate to give 1-(2,4-dimethylphenyl)-3-methyl-5-(2-N-methyl-thiocarbamoyloxyethyl)-tetrahydro-s-triazin-2[1H]-thione, m.p. 82°-90° C.

Analysis %: Found: C, 55.1; H, 7.0; N, 15.3 $C_{21}H_{26}N_4OS_2$ requires: C, 54.5; H, 6.8; N, 15.9.

EXAMPLE 28

The method of Example 26 was followed using phenyl isothiocyanate to give 1-(2,4-dimethylphenyl)-3-methyl-5-(2-N-phenylthiocarbamoyloxyethyl)-tetrahydro-s-triazin-2[1H]-thione, m.p. 64°-70° C.

Analysis %: Found: C, 60.9; H, 6.3; N, 13.7 $C_{21}H_{26}N_4OS_2$ requires: C, 60.9; H, 6.3; N, 13.5.

EXAMPLE 29

A solution of p-tolunesulphonyl chloride (3.0 g) in pyridine (5 ml) was added slowly to a cold stirred solution of 1-(2,4-dimethylphenyl)-5-(2-hydroxyethyl)-3-methyl-tetrahydro-s-triazin-2[1H]-thione (1.5 g, 1.8 mmole) in pyridine (10 ml). Stirring was continued for a further 10 minutes and the solution was allowed to stand overnight at 3° C. The solution was poured into ice/water (400 ml) and the product extracted into ether (2×100 ml). The combined ethereal extracts were washed with dilute hydrochloric acid and with water and dried. The solvent was removed and the residual gum was taken up in ethyl acetate. The solution was chilled and petroleum ether (b.p. 40°-60° C.) added slowly to give 1-(2,4-dimethylphenyl-3-methyl-5-(p-toluenesulphonyloxyethyl)-tetrahydro-s-triazin-2[1H]-thione as a white solid (0.9 g, 58%), m.p. 82°-85° C.

Analysis %: Found: C, 58.4; H, 6.3; N, 9.6 $C_{21}H_{27}N_3S_2$ requires: C, 58.2; H, 6.2; N, 9.7%.

EXAMPLE 30

Aqueous formaldehyde (3.6 g, 4 mmole) was added to a suspension of N-2,4-dimethylphenyl-N'-methyl-thiourea (1.76 g, 2 mmole) in ethylene glycol (500 ml) followed by slow addition of a solution of N,N-dimethyl-ethylenediamine (1.76 g, 2 mmole) in a little ethylene glycol. The mixture was heated for 1 hour at 80°-90° C. and then cooled and poured into water. The product was extracted with ether, the ether layer separated, washed with water, dried and evaporated. The crude product was chromatographed on a column of silica eluting with dichloromethane containing 3% methanol to yield an oil which solidified on trituration with petroleum ether (b.p. 40°-60° C.) to give 1-(2,4-dimethylphenyl)-3-methyl-5-dimethylaminoethyl-tetrahydro-s-triazin-2[1H]-thione (0.6 g, 20%), m.p. 65°-70° C.

Analysis %: Found: C, 62.25; H, 8.6; N, 17.8 $C_{16}H_{26}N_4S$ requires: C, 62.7; H, 8.5; N, 18.3%.

EXAMPLE 31

A solution of hydrogen chloride in ether was added to an ether solution of 1-(2,4-dimethylphenyl)-3,5-dimethyltetrahydro-s-triazin-2[1H]-thione. The mixture was allowed to stand in the cold for 1 hour and the precipitated hydrochloride salt was collected, washed with a little cold ether and dried, m.p. 164°-165° C.

Analysis %: Found: C, 54.45; H, 7.6; N, 15.2; Cl, 12.6 $C_{13}H_{19}N_3S \cdot HCl$ requires: C, 54.6; H, 7.0; N, 14.7; Cl, 12.4%.

What is claimed is:

1. A compound selected from the group consisting of

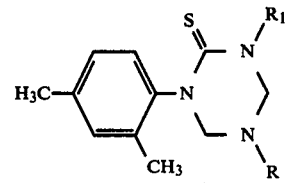

and a pharmaceutically acceptable acid addition salt thereof, wherein R is selected from the group consisting of alkyl having from one to twelve carbon atoms, cycloalkyl having from three to six carbon atoms, adamantyl, benzyl, allyl, propargyl and substituted alkyl wherein said alkyl contains from two to four carbon atoms and said substituent is selected from the group consisting of hydroxy, alkoxy having from one to three carbon atoms, alkanoyloxy having from two to five carbon atoms, methylamino, dimethylamino, phenyl, p-toluenesulfonyloxy and carbamoyloxy of the formula

wherein $R_2$ is selected from the group consisting of hydrogen, cyclohexyl, phenyl and methyl and Q is selected from the group consisting of oxygen and sulphur, with the proviso that said substituent is substituted on other than the alpha-position of said substituted alkyl; and $R_1$ is selected from the group consisting of alkyl having from one to three carbon atoms and hydroxymethyl.

2. A compound of claim 1 wherein $R_1$ is methyl and R is alkyl having from one to twelve carbon atoms.

3. The compound of claim 2 wherein R is methyl.

4. The compound of claim 2 wherein R is i-propyl.

5. The compound of claim 2 wherein R is t-butyl.

6. A method for protecting cattle from acarids which comprises applying externally to said cattle in need of such protection an acaricidal amount of a compound selected from the group consisting of

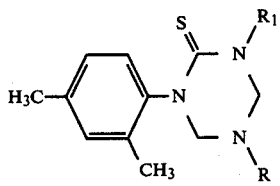

and a pharmaceutically acceptable addition salt thereof, wherein

R is selected from the group consisting of alkyl having from one to twelve carbon atoms, cycloalkyl having from three to six carbon atoms, adamantyl, benzyl, allyl, propargyl and substituted alkyl wherein said alkyl contains from two to four carbon atoms and said substituent is selected from the group consisting of hydroxy, alkoxy having from one to three carbon atoms, alkanoyloxy having from two to five carbon atoms, methylamino, dimethylamino, phenyl, p-toluenesulfonyloxy and carbamoyloxy of the formula

wherein $R_2$ is selected from the group consisting of hydrogen, cyclohexyl, phenyl and methyl and Q is selected from the group consisting of oxygen and sulphur, with the proviso that said substituent is substituted on other than the alpha-position of said substituted alkyl; and $R_1$ is selected from the group consisting of alkyl having from one to three carbon atoms and hydroxymethyl.

7. The method of claim 6 wherein $R_1$ is methyl and R is alkyl having from one to twelve carbon atoms.

8. The method of claim 7 wherein R is methyl.

9. The method of claim 7 wherein R is i-propyl.

10. The method of claim 7 wherein R is t-butyl.

11. An acaricidal composition comprising an effective amount of a compound of the formula

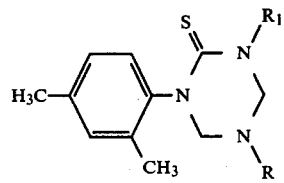

and a pharmaceutically acceptable acid addition salt thereof, wherein R is selected from the group consisting of alkyl having from one to twelve carbon atoms, cycloalkyl having from three to six carbon atoms, adamantyl, benzyl, allyl, propargyl and substituted alkyl wherein said alkyl contains from two to four carbon atoms and said substituent is selected from the group consisting of hydroxy, alkoxy having from one to three carbon atoms, alkanoyloxy having from two to five carbon atoms, methylamino, dimethylamino, phenyl, p-toluenesulfonyloxy and carbamoyloxy of the formula

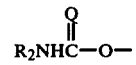

wherein $R_2$ is selected from the group consisting of hydrogen, cyclohexyl, phenyl and methyl and Q is selected from the group consisting of oxygen and sulphur, with the proviso that said substituent is substituted on other than the alpha-position of said substituted alkyl; and.

$R_1$ is selected from the group consisting of alkyl having from one to three carbon atoms and hydroxymethyl.

12. A composition of claim 11 wherein $R_1$ is methyl and R is alkyl having from one to twelve carbon atoms.

13. The composition of claim 12 wherein R is methyl.

14. The composition of claim 12 wherein R is i-propyl.

15. The composition of claim 12 wherein R is t-butyl.

* * * * *